(12) United States Patent
Meyer

(10) Patent No.: US 11,534,276 B2
(45) Date of Patent: Dec. 27, 2022

(54) METHOD AND DEVICE FOR FUNCTIONALISING DENTAL RESTORATIONS

(71) Applicant: bredent GmbH & Co. KG, Senden (DE)

(72) Inventor: Joachim Meyer, Ulm (DE)

(73) Assignee: bredent GmbH & Co. KG, Senden (DE)

( * ) Notice: Subject to any disclaimer, the term of this patent is extended or adjusted under 35 U.S.C. 154(b) by 960 days.

(21) Appl. No.: 16/331,201

(22) PCT Filed: Sep. 15, 2017

(86) PCT No.: PCT/EP2017/073257
§ 371 (c)(1),
(2) Date: Mar. 7, 2019

(87) PCT Pub. No.: WO2018/050811
PCT Pub. Date: Mar. 22, 2018

(65) Prior Publication Data
US 2019/0274797 A1      Sep. 12, 2019

(30) Foreign Application Priority Data
Sep. 15, 2016   (DE) .................... 10 2016 117 395.9

(51) Int. Cl.
| | |
|---|---|
| *A61C 13/00* | (2006.01) |
| *B05D 5/06* | (2006.01) |
| *A61C 13/083* | (2006.01) |
| *A61K 6/78* | (2020.01) |
| *A61K 6/818* | (2020.01) |

(Continued)

(52) U.S. Cl.
CPC ...... *A61C 13/0006* (2013.01); *A61C 13/0004* (2013.01); *A61C 13/083* (2013.01); *A61K 6/78* (2020.01); *A61K 6/818* (2020.01); *A61K 6/849* (2020.01); *A61C 5/77* (2017.02); *A61C 13/0022* (2013.01); *A61C 13/082* (2013.01);
(Continued)

(58) Field of Classification Search
CPC .............................. A61C 13/0006; B05D 5/06
USPC ................................................ 427/256, 2.27
See application file for complete search history.

(56) References Cited

U.S. PATENT DOCUMENTS 5,910,273 A * 6/1999 Thiel .................. A61C 13/0003
                                                        264/16
6,709,694 B1 * 3/2004 Suttor ..................... A61K 6/818
                                                        427/372.2
(Continued)

FOREIGN PATENT DOCUMENTS

DE    10 2010 037 160 A1    3/2012
DE    10 2011 117005 A1    4/2013
(Continued)

OTHER PUBLICATIONS

International Search Report in PCT/EP2017/073257, dated Jan. 5, 2018.

*Primary Examiner* — Cachet I Proctor
(74) *Attorney, Agent, or Firm* — Collard & Roe, P.C.

(57) ABSTRACT

In a functionalization method for use in dentistry, and a method for same, the application device includes a support for receiving a partially processed shaped dental part for producing a dental restoration, and a dispensing device for the at least partial infiltration of a functionalization material onto the surface of the shaped dental part.

15 Claims, 2 Drawing Sheets

Figure 1:
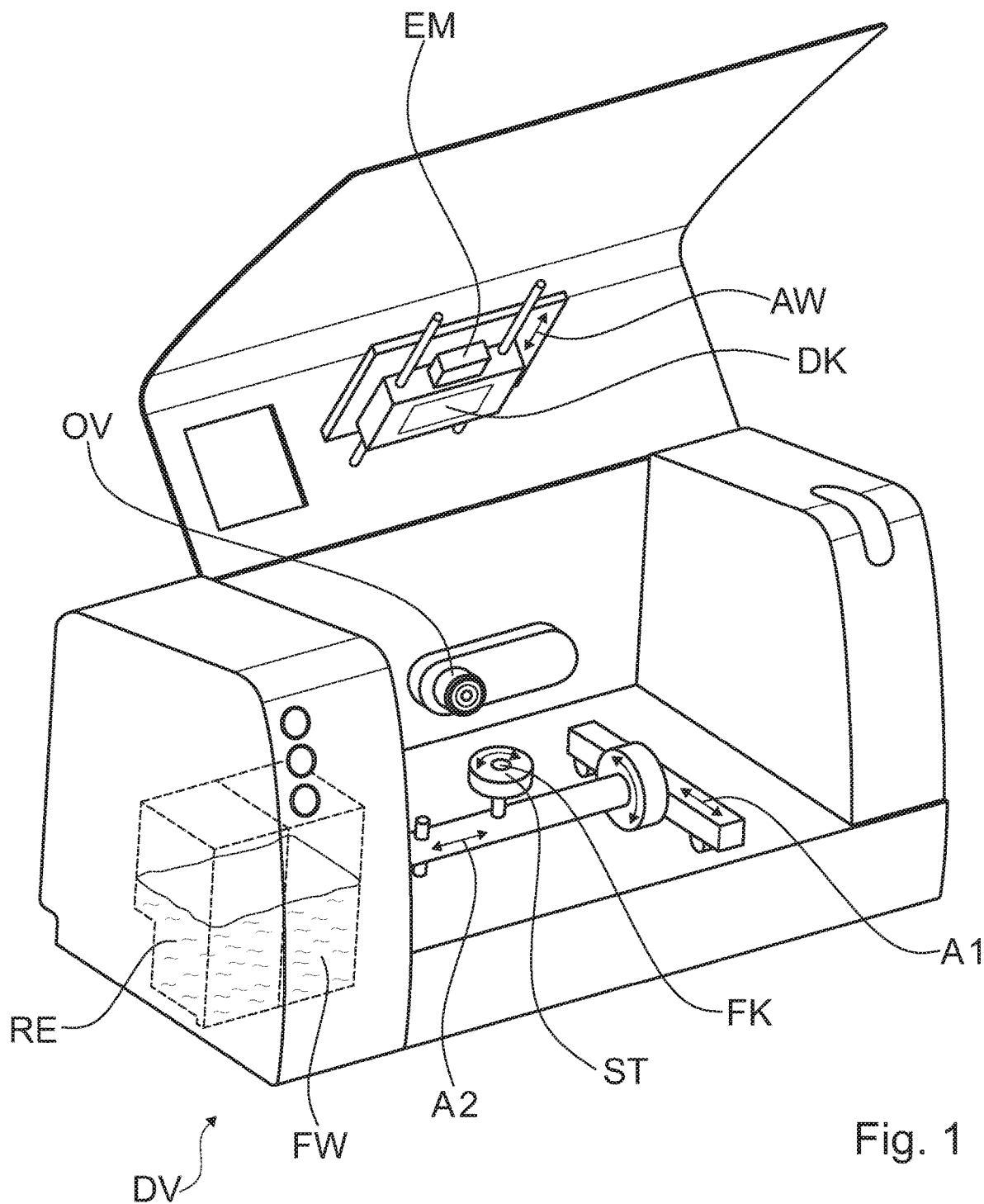

(51) Int. Cl.
*A61K 6/849* (2020.01)
*A61C 5/77* (2017.01)
*A61C 13/08* (2006.01)
*C04B 41/00* (2006.01)
*C04B 111/00* (2006.01)
*A61K 6/30* (2020.01)

(52) U.S. Cl.
CPC .............. *A61K 6/30* (2020.01); *C04B 41/009* (2013.01); *C04B 2111/00836* (2013.01)

(56) References Cited

U.S. PATENT DOCUMENTS

| | | | |
|---|---|---|---|
| 7,932,743 B1* | 4/2011 | Stewart | H03K 19/17756 326/38 |
| 8,080,189 B2 | 12/2011 | Rothbrust et al. | |
| 10,292,795 B2* | 5/2019 | Herrmann | A61K 6/811 |
| 2004/0245663 A1* | 12/2004 | MacDougald | A61K 6/818 264/16 |
| 2007/0077534 A1* | 4/2007 | Saliger | B22F 3/26 433/167 |
| 2010/0260924 A1* | 10/2010 | Karim | A61C 13/082 427/2.26 |
| 2012/0052186 A1* | 3/2012 | Junglas | A61C 13/09 118/696 |
| 2014/0101869 A1* | 4/2014 | Carden | A61K 6/78 8/645 |
| 2014/0178834 A1* | 6/2014 | Jahns | A61K 6/849 106/35 |
| 2016/0157971 A1* | 6/2016 | Rothbrust | C04B 35/486 264/16 |
| 2017/0157645 A1* | 6/2017 | Wolz | C04B 41/5048 |
| 2017/0319305 A1* | 11/2017 | Rolf | A61C 5/70 |

FOREIGN PATENT DOCUMENTS

| | | | | |
|---|---|---|---|---|
| EP | 1 911 568 A1 | 4/2008 | | |
| EP | 1911568 A1 * | 4/2008 | ......... | A61C 13/0019 |
| EP | 1 153 002 B1 | 9/2014 | | |
| JP | 2005-059477 A | 3/2005 | | |
| WO | 2005/070322 A1 | 8/2005 | | |
| WO | 2014/206439 A1 | 12/2014 | | |
| WO | WO-2014206439 A1 * | 12/2014 | ......... | A61C 13/0004 |

* cited by examiner

METHOD AND DEVICE FOR FUNCTIONALISING DENTAL RESTORATIONS

CROSS REFERENCE TO RELATED APPLICATIONS

This application is the National Stage of PCT/EP2017/073257 filed on Sep. 15, 2017, which claims priority under 35 U.S.C. § 119 of German Application No. 10 2016 117 395.9 filed on Sep. 15, 2016, the disclosure of which is incorporated by reference. The international application under PCT article 21(2) was not published in English.

The invention relates to a method for functionalization of dental restorations, and to an apparatus for functionalization of dental restorations.

New types of production methods for permanent restorations are being developed, above all, with regard to ceramic materials and ceramic/hybrid materials. Furthermore, monolithic ceramic materials composed of highly transparent zirconium dioxide are usual on the market. These materials are produced in shaping processes, in fully anatomical manner, in subtractive processing forms, for example by means of chip-removing or grinding, as well as in additive methods, for example by means of thermodynamic pressing techniques.

A method for production of an inorganic/inorganic composite material is known from WO 2005/070322 A1, in which method an open-pore, crystalline oxide ceramic shaped part is produced from an oxide ceramic powder or from a powder of an oxide ceramic mixture, after shaping processing and pre-sintering, an infiltration material is applied to this part under a vacuum and at room temperature, and the oxide ceramic is sintered, compacting it, under air atmosphere and ambient pressure, to form an inorganic/inorganic composite material.

It is furthermore known that white compacts composed of zirconium dioxide are infiltrated with a liquid that contains metal oxide before they are sintered, so as to achieve individual coloration. Another approach is to make semi-finished products composed of polychrome gradients available, so as to imitate the color progression of a natural tooth.

For example, coloration of ceramics by means of ionic solutions or solutions containing complexes is described in EP 1 153 002 A1. Solutions suitable for this purpose contain defined concentrations of the salts or complexes of the rare earth elements or of the elements of the transition groups.

A method for coloration of ceramics that contain binders and/or from which binders have been removed and/or that are partially sintered and/or that are porous throughout, in particular of porous ceramic shaped bodies, which are particularly used in dental technology, is described in WO 2014/206439 A1, wherein the color application takes place with an application tool and/or pin-type tool, which has the composite material, in particular the painting pin composite material, mixed with color-imparting components and/or refractory pigments and/or oxides and/or color-imparting and fluorescent metal oxides and/or organic or inorganic salts.

A disadvantage of the known infiltration technique is that these liquids are applied by hand and therefore it cannot be precisely defined by means of material absorption where the color gradients lie or where separations exist and how strongly the infiltration controls the color saturation, since these liquids only experience the desired color development with regard to intensity and color depth (chroma) as the result of the thermal treatment of sintering. Due to the very different color regions of a crown/bridge, differentiating infiltration with precise color structuring is not possible. The very different material thicknesses within a crown/bridge, due to anatomical conditions, lead to very different absorption and saturation behavior. Due to this property, suitable infiltrations or functionalizations of surfaces or solid regions cannot be precisely defined.

The product solution mentioned above, of polychromatic layering of semi-finished products, has the disadvantage that in the case of a concave occlusion progression of crowns/bridges, the color gradients in the semi-finished product do not run in curved manner but rather horizontally. As a result, non-uniform, unnatural color progressions occur.

The common set of problems of these different product solutions is that reproducible, individual color structuring is not possible. A further disadvantage in the case of the colored semi-finished products is that the customer must reproduce a color key of typically at least sixteen polychromatic tooth colors and therefore must use semi-finished products in accordance with the respective requirements, and this is very time-intensive and requires keeping a large inventory.

A method for the production of tooth replacements is described in DE 10 2010 037 160 A1, in which multiple layers of a material mixture are applied to a carrier structure as a function of a digital model of the tooth replacement, for production of a veneer. In this regard, specific layers of the layers, which are applied directly one on top of the other, can also have a coloration. For orientation or positioning of the carrier, a holder is provided, which is positioned as a function of control commands.

A digital printing process is described in US 2010/0260924 A1, which process is used for functionalization of a surface of a dental replacement. In this regard, a multi-color surface can be produced, which is adapted to the original teeth in terms of color.

However, it appears to be a disadvantage of these methods that during production, complex layer applications or compound applications come about, which change the volume and require complex production systems and production times. Furthermore, an increase in the size of the surface comes about due to the superficial material application (for example of the color), which must later be adapted to the occlusion conditions by hand. Here, in turn, removal of the superficial color layer must be expected as the result of required corrections.

Based on the advancing Rapid Prototyping method, different material properties and color-imparting systems are required, so as to achieve a maximum in terms of production and color-sure and individual reproduction here, with a very small selection of basic materials/colors.

It is therefore the task of the invention to create a method for functionalization of dental restorations and an apparatus for functionalization of dental restorations, which allow versatile modification of surfaces.

This task is accomplished by the independent claims 1 and 10. Further advantageous embodiments of the invention are the object of the dependent claims, in each instance. These can be combined with one another in technologically practical manner. The description, in particular in connection with the drawing, additionally characterizes and specifies the invention.

According to the invention, in a first aspect a method for surface functionalization of dental restorations is indicated, in which the following steps are carried out: insertion of a shaped body into a holder of an application apparatus, provision of a digital data set that represents at least a partial region of the surface of the dental shaped body, selection of a functionalization surface within the partial region of the surface of the dental shaped body, infiltration of a volume under the functionalization surface with an active functionalization substance, wherein the infiltration takes place with the active functionalization substance by means of targeted movement of the holder and/or of a dispensing apparatus, and the infiltration brings about an increase in mass of the shaped body with an essentially unchanged volume of the shaped body, and removal of the dental shaped body from the application apparatus, and activation of the active functionalization substance in a thermal, optical or chemical process.

Accordingly, it is possible, according to the invention, to capture three-dimensional surfaces digitally and to process them, thereby making functionalization possible, using a coating method, by means of suitable active substances, so as to treat the surface accordingly. In this regard, production methods and materials already usual on the market can be subsequently processed further digitally. The method of procedure according to the invention makes it possible to process the surface digitally and to absorb the functionalization substances used in this regard in the volume body for the purpose of changing the optical, mechanical or physical properties.

This has the advantage that no small production batches need to be compiled within the Rapid Prototyping method, which would not be efficient with regard to the efficiency and production capacity and technical design of these systems. Ceramic basic material can be printed, pressed or milled for the shaped body, independent of what subsequent individual functionalization of the respective dental restoration in the form of a crown or bridge is desired. The advantage here is that using the Rapid Prototyping method, only large production batches can be pre-produced, and these are subsequently subjected to individual functionalization.

In contrast to a purely superficial color application, as it was already described in the state of the art, here digitally guided surface functionalization is carried out by means of infiltration of ceramics, wherein here, no superficial application with a volume increase of layers takes place, but rather absorption of the active functionalization substance with a mass increase takes place, and thereby this absorption functionalizes the infiltrated layer/compound with the desired properties.

According to an embodiment of the invention, the shaped body is made available as a porous ceramic, open ceramic, white ceramic, green ceramic, green compact or monolithic ceramic, or processed from a semi-finished product consisting thereof, by means of a pressing process, by means of a shaping casting process, or in a mold-free 3D printing process.

According to the invention, automated processing by machine of ceramics that have already been processed, i.e. of dental technology restorations, which were already processed further from a semi-finished product or produced in a pressing process, is undertaken.

In this regard, according to a further embodiment of the invention, a color application, a light-curing varnish, a cold silane, a resin infiltration or a superficial application of ceramic or polymer glazes, metal oxides or rare earths can be applicable as an active functionalization substance to change the optical properties.

A suitable active functionalization substance can be introduced by way of the surface, by means of infiltration, into the volume that lies underneath, wherein a superficial application onto structures that have already been sintered and fired or onto partially or fully polymerized polymers is conceivable. This includes application of optical changes such as brightness or opalescence, chemical functionalities with regard to optimization of adhesion composites, physical properties with regard to optimization of material properties by means of surface coating and infiltration such as hardness, elasticity or a change in the heat expansion coefficient by means of introduction of leucite into ceramics.

For color adaptation, it is possible, for example, to now pre-produce large production batches, without sorting these, as was previously done, into small production batches using the division into the sixteen polychrome tooth colors. By means of the invention, it is now possible to compile and produce a common production batch, independent of the subsequent different and individual functionalization, also of partial regions, which is subsequently subjected to individual functionalization, using the coating process.

By means of a CMYK-based color system, it would be possible to produce all tooth colors. Here, the current typical dental color systems are composed of the classically based or derived tooth color assignments of the "VITA classical" color system. Grouping of the colors in the "VITA classical" color system takes place according to color tones and their distribution in the tooth color space: A1-A4 reddish-brownish, B1-B4 reddish-yellowish, C1-C4 gray tones, and D2-D4 reddish-gray. A CMYK-based color system would therefore be based on printing technology, wherein colors can be described independent of apparatus.

According to a further embodiment of the invention, the dispensing apparatus of the application apparatus is structured as a print head, as a spray head or as an application unit based on contact-related printing.

This allows application of the liquid active functionalization substance similar to a printer. In this regard, the liquid can be printed on or also sprayed on, or imprinted in contact-related manner. The desired amount or thickness can be applied locally by means of control of the dispensing apparatus on the application apparatus. Application of the liquid active functionalization substance leads to penetration into the shaped body, so that this body experiences an increase in mass, but not an increase in volume.

According to a further embodiment of the invention, the digital data set is taken over into the application apparatus by means of spatial transfer and assignment to the correct position.

It is advantageous here that the digital surface data set created with regard to the physical shaped body, which set was captured externally in advance, for example, is taken over into the application apparatus by means of spatial transfer and assignment, to the correct position, of the different spatial coordinate systems of the external measurement apparatus. Thus, for example, triangulation of a physical body could be undertaken, from which the corresponding control commands for the application apparatus are then derived.

According to a further embodiment of the invention, the digital data set is determined by way of an internal or external measurement apparatus, which captures the surface of the dental shaped body in tactile, optical or acoustical manner.

Aside from a measurement apparatus that can carry out a surface determination in different physical ways, it is also provided, according to the invention, to provide the measurement apparatus as an external unit or, alternatively, within the application apparatus.

According to a further embodiment of the invention, the measurement apparatus is configured as a camera or as a three-dimensional scanner.

The surface of the shaped body can be captured by means of a camera or a scanner. Possibly, no camera might be present for surface capture, but these surface data sets could be transferred to a separate measurement unit for surface capture using zero-point assignment of the scanner, and to the application apparatus as data, by means of a zero-chip apparatus.

According to a further embodiment of the invention, a color measurement is additionally carried out on the surface of the shaped body by means of a digital system.

An optical measurement apparatus for surface capture will typically have a lens that is not intended or optimized for color measurement. Accordingly, a special lens would have to be installed, which is separate from the lens used for three-dimensional capture of the surface.

According to a further embodiment of the invention, a remote measurement takes place, so as to adjust a distance during application of the active functionalization substance or to determine a reference point.

The determination of the reference point furthermore also allows positioning of the dental restoration or of the carrier relative to the zero point.

According to a further embodiment of the invention, the application apparatus will approach defined surfaces, proceeding from the digital data set, and will control application of the active functionalization substance with regard to the materials used, their thicknesses or densities.

In this regard, application can be coordinated within a five-axis processing in all three spatial axes, so as to achieve undercuts on the dental restoration here, as well.

In a second aspect, an application apparatus for carrying out a method for functionalization of dental restorations is indicated, in particular according to methods as described above, comprising a contact surface for holding a partially processed dental shaped body for the production of a dental restoration and a dispensing apparatus for spatially predefined infiltration, at least in certain sections, of a liquid active functionalization substance in a volume below a surface of the dental shaped body assigned by way of a digital data set, wherein the infiltration brings about a mass increase of the shaped body with an essentially unchanged volume of the shaped body.

The application apparatus allows application of an active functionalization substance in a pre-determined surface region, wherein the infiltrated volume, the layer thickness, and other parameters can be precisely controlled during application. For this purpose, a digital data set is made available, which serves as a basis for application of a liquid active functionalization substance to a surface of the dental shaped body, which surface is assigned by way of a digital data set.

According to a further embodiment of the invention, the contact surface can be moved along multiple axes, preferably can be displaced along a first axis and a second axis and can be rotated along the second axis and/or a third axis, and application of the active functionalization substance takes place by means of targeted movement of the contact surface. In this regard, the dispensing apparatus can be moved along at least one further axis, and application of the active functionalization substance can take place by means of targeted movement of the dispensing apparatus.

Accordingly, a possibility is created of impacting an individually definable surface selection on the surface of the dental shaped body and of processing this by machine, with reproducible parameters, in that an application of defined amount on defined surfaces takes place by means of application of the active functionalization substance. Thus, for example, the homogeneities to be achieved with regard to the layer thickness to be applied or the material density and the material thickness of the active functionalization substance can be controlled in precise manner, so that based on the material properties of the active functionalization substance, no different results are brought about after infiltration into the volume that lies underneath, as would be expected in the case of an uncontrolled analog use by means of manual application. Individual material properties can be taken into consideration as processing parameters (material, density, material thickness) of the active functionalization substance by means of digital processing, and can thereby be compensated.

Furthermore, a software program product is indicated, which contains commands that can be read by a processor, which commands are suitable for carrying out a method described above.

Finally, a control device of an application apparatus is indicated, which receives commands from a memory, which commands are suitable for carrying out a method described above.

Figure 2:
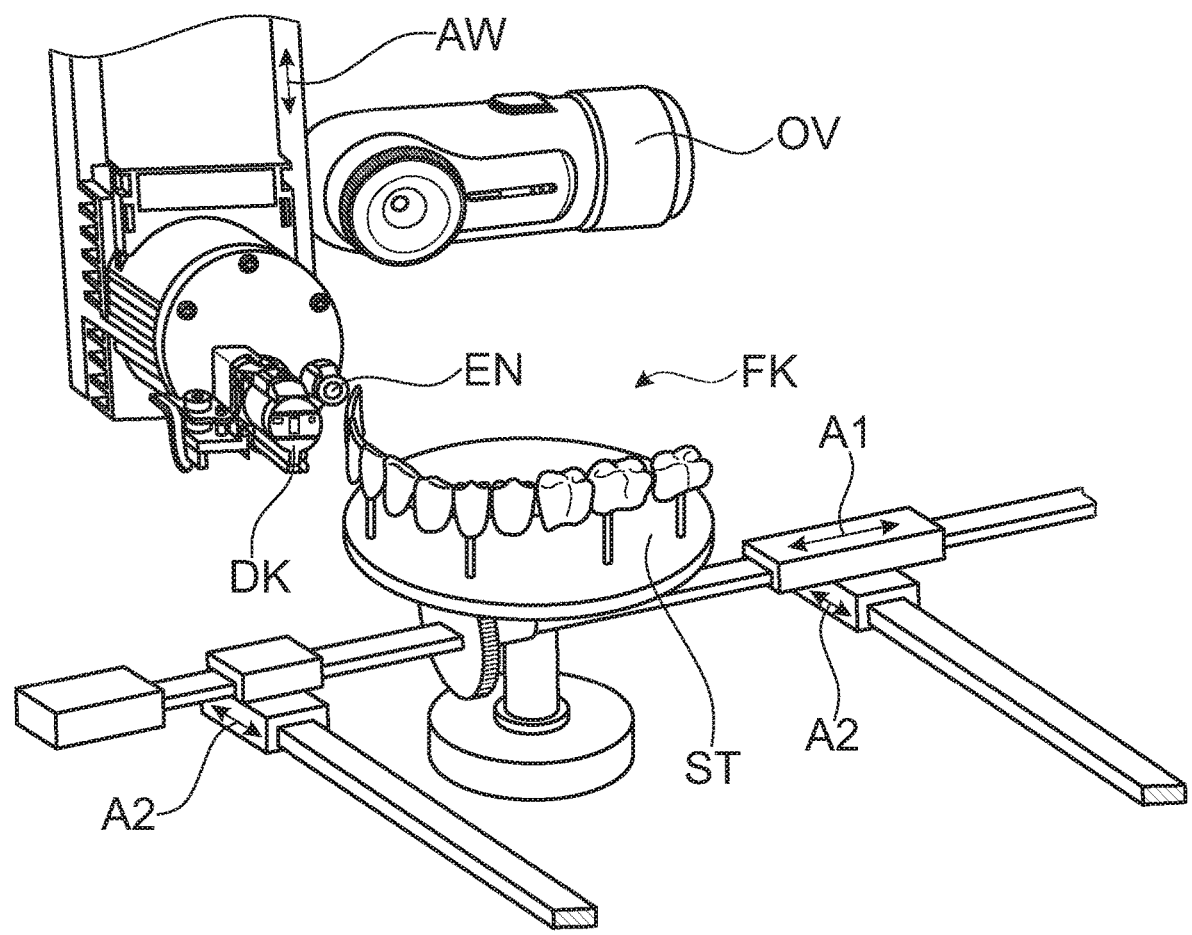

In the following, some exemplary embodiments will be explained in greater detail using the drawing. This shows:

FIG. 1 a perspective side view of an application apparatus for use of the method according to the invention, and FIG. 2 a detail view of the application apparatus from FIG. 1.

In the figures, components that are the same or have the same functional effect are provided with the same reference symbols.

In FIG. 1, a three-dimensional representation of an application apparatus DV for surface functionalization for dental uses is shown in a perspective side view. The application apparatus DV has a contact surface in the form of a scanning table ST, which can be rotated along an axis perpendicular to the contact surface. Furthermore, the scanning table ST can be displaced along a first axis A1 provided as an X axis and along a second axis A2 provided as a Y axis. Furthermore, the scanning table can also be rotated about the second axis A2. Displacement along the first axis A1 and the second axis A2 as well as rotation about the second axis A2 or perpendicular to the holding surface can be controlled by means of suitable stepper motors (not shown in FIG. 1).

A shaped body FK is placed onto the scanning table ST. The shaped body FK can have an anatomical outer surface or can be made available as a framework. In general, it holds true that the shaped body FK is used for the production of a dental restoration. In this regard, the shaped body FK is typically processed from a semi-finished product or produced by means of a pressing process.

The shaped body FK is captured in three dimensions by means of a measurement apparatus OV, so that the surface of the shaped body FK can be processed further digitally. In this regard, capture of the surface can take place optically but also in tactile or acoustical manner. In the case of acoustical measurement by means of sonar or sound waves, neither movements nor multiple spatial axes are required. However, capture of the surface of the shaped body can also take place outside of the measurement apparatus OV, using a device suitable for this purpose.

For section-by-section application of an active functionalization substance, which can be taken from a reservoir RE, for example, a dispensing apparatus in the form of a print head DK is provided, which stands in connection with the reservoir RE for feed of the active functionalization substance FW. The print head DK can also be moved along a further axis AW, which can be selected, for example, perpendicular to the first axis A1 and perpendicular to the second axis A2, as a Z axis. The axes can also be disposed completely differently. For example, the camera does not need to be disposed on the lid and can be affixed differently; the same holds true for the print head. In this regard, application can be coordinated in all three spatial axes within five-axis processing, so as to achieve undercuts on the dental restoration here, as well.

Application of the active functionalization substance FW now takes place by means of targeted movement of the scanning table ST and, if applicable, of the print head DK. In this regard, the movements of both the print head DK and of the scanning table ST can be coordinated by means of a suitable control apparatus, so that a desired partial section on the surface of the shaped body FK is provided with the active functionalization substance FW. The print head DK can typically be structured as an ink-jet head or as a spray head.

In general, the surface can be coated with a suitable active functionalization substance, wherein, for example, superficial application onto structures that have already been sintered and fired or onto partially or completely polymerized polymers is conceivable. This includes application of optical changes such as brightness or opalescence, chemical functionalities with regard to optimization of adhesive composites, physical properties with regard to optimization of material properties by means of surface coating and infiltration, such as hardness, elasticity or a change in heat expansion coefficients by means of introduction of leucite into ceramics. Application of the liquid active functionalization substance leads to penetration into the shaped body, so that the latter experiences an increase in mass but not in volume.

The measurement apparatus can be configured as a camera or as a three-dimensional scanner, for example as a laser scanner or as a structured light scanner. The measurement apparatus can also have a tactile or acoustical unit in place of or in addition to the camera.

Furthermore, a distance meter EM is provided, which determines a distance between the print head DK and the shaped body FK. In this regard, the distance meter EM can check or adjust the distance from the print head DK during application of the active functionalization substance, but can also be used to determine a reference point, for example a zero point or starting point at the beginning of application or at the beginning of scanning of the surface of the shaped body FK.

Furthermore, it is provided to expand the measurement apparatus OV with a color measurement. For the color measurement, a special lens would have to be installed, which is separate from the lens used for three-dimensional capture of the surface.

The measurement apparatus OV is preferably coupled with corresponding processing software, which represents the surface of the shaped body FK accordingly after three-dimensional optical capture. The surface of the shaped body FK can now be processed within the processing software, wherein the further processing depends on the desired functionalization. For example, it is possible to individually color the surface of the shaped body FK digitally, wherein here, the digital system mentioned above is used for color measurement.

After digital processing of the surface, the printing process by means of the print head DK is started. In this regard, it is also conceivable to use different active functionalization substances successively.

After the printing process has been concluded, the printed shaped body FK is removed from the application apparatus DV and activated in a subsequent thermal, optical or chemical process.

A detail of the application apparatus DV for surface functionalization is shown in FIG. 2. It can be seen that the application apparatus DV has the contact surface in the form of a scanning table ST, which can be rotated along an axis perpendicular to the contact surface. A dental restoration FK is laid onto the scanning table.

The scanning table ST can be displaced along the first axis A1, provided as an X axis, or along the second axis A2, provided as a Y axis. Furthermore, the scanning table can also be rotated about the second axis A2. Displacement along the first axis A1 and the second axis A2 as well as rotation about the second axis A2 or perpendicular to the holding surface can be controlled by means of suitable stepper motors (not shown in FIG. 2). In general, it holds true that the shaped body FK is used for production of a dental restoration. In this regard, the shaped body FK has typically been processed from a semi-finished product or produced by means of a pressing method.

The shaped body FK is captured by means of the measurement apparatus OV, so as to determine its three-dimensional surface. In addition, a color measurement by means of a digital system (not shown in FIG. 2) can be carried out on the surface of the shaped body FK. Furthermore, a distance measurement takes place by way of a distance or spacing meter EN, so as to adjust a distance relative to the dispensing apparatus in the form of the print head DK during application of the active functionalization substance or to determine a reference point. Determination of the reference point furthermore also allows positioning of the dental restoration in the form of the shaped body FK or of the carrier ST with regard to a zero point.

The characteristics indicated above and in the claims as well as those that can be derived from the figures can be advantageously implemented both individually and in different combinations. The invention is not restricted to the exemplary embodiments described, but rather can be modified in many ways within the scope of the ability of a person skilled in the art.

The invention claimed is:

1. A method for functionalization of dental restorations, in which the following steps are carried out:
 inserting a shaped body into a holder of an application apparatus,
 providing a digital data set that represents at least a partial region of the surface of the shaped body,
 selecting a functionalization surface within the partial region of the surface of the shaped body,
 infiltrating a volume under the functionalization surface with a liquid active functionalization substance by applying the liquid active functionalization substance, which leads to penetration into the shaped body, wherein the infiltrating takes place with the active functionalization substance by targeted movement of the holder and/or of a dispensing apparatus, and the infiltrating brings about an increase in mass of the shaped body with an essentially unchanged volume of the shaped body,
 removing the shaped body from the application apparatus, and activating the active functionalization substance in a thermal, optical or chemical process.

2. The method according to claim 1, in which the shaped body is made available as a porous ceramic, open ceramic, white ceramic, green ceramic, green compact or monolithic ceramic, or processed from a semi-finished product comprising porous ceramic, open ceramic, white ceramic, green ceramic, green compact or monolithic ceramic, using a pressing process, using a shaping casting process, or in a mold-free 3D printing process.

3. The method according to claim 1, further comprising an active functionalization substance to change optical properties of the shaped body comprising a color application, a light-curing varnish, a cold silane, a resin infiltration or a superficial application of ceramic or polymer glazes, metal oxides or rare earths.

4. The method according to claim 1, in which the application apparatus is a dispensing apparatus that has a print head, a spray head or an application unit based on contact-related printing.

5. The method according to claim 1, in which the digital data set is taken over into the application apparatus by means of spatial transfer and assignment to the correct position.

6. The method according to claim 1, in which the digital data set is determined by way of an internal or external measurement apparatus, which captures the surface of the shaped body in tactile, optical or acoustical manner.

7. The method according to claim 6, in which the measurement apparatus is configured as a camera or as a three-dimensional scanner.

8. The method according to claim 1, in which a color measurement is additionally carried out on the surface of the shaped body by means of a digital system.

9. The method according to claim 1, in which a remote measurement takes place, so as to adjust a distance during application of the active functionalization substance or to determine a reference point.

10. The method according to claim 1, in which the application apparatus will approach defined surfaces, proceeding from the digital data set, and can control infiltration of the active functionalization substance with regard to the materials used, their thicknesses or densities.

11. An application apparatus for carrying out the method for functionalization of dental restorations according to claim 1, comprising a contact surface for holding a partially processed shaped body for the production of a dental restoration and a dispensing apparatus for application of a liquid active functionalization substance, which penetrates into the shaped body, and spatially pre-defined infiltration, at least in certain sections, of the liquid active functionalization substance in a volume below a surface of the shaped body assigned by way of a digital data set, wherein the infiltration brings about a mass increase of the shaped body with an essentially unchanged volume of the shaped body.

12. The application apparatus according to claim 11, in which the contact surface can be displaced along a first axis and a second axis and can be rotated along the second axis and/or a third axis, and application of the active functionalization substance takes place by targeted movement of the contact surface.

13. The application apparatus according to claim 12, in which the dispensing apparatus can be moved along at least one further axis, and application of the active functionalization substance takes place by targeted movement of the dispensing apparatus.

14. A software program product, which contains commands that can be read by a processor, which commands are suitable for carrying out the method according to claim 1.

15. A control device of an application apparatus, which receives commands from a memory for carrying out the method according to claim 1.

* * * * *